United States Patent [19]
Herbst et al.

[11] Patent Number: 5,242,474
[45] Date of Patent: Sep. 7, 1993

[54] DUAL MODE LASER SMOKE EVACUATION SYSTEM WITH SEQUENTIAL FILTER MONITOR AND VACUUM COMPENSATION

[75] Inventors: Royce Herbst, Riverton; James L. Sorenson, Salt Lake City, both of Utah

[73] Assignee: Sorenson Laboratories, Inc., Salt Lake City, Utah

[21] Appl. No.: 974,378

[22] Filed: Nov. 10, 1992

Related U.S. Application Data

[63] Continuation of Ser. No. 706,455, Nov. 1, 1991, abandoned.

[51] Int. Cl.⁵ ............................................. B01D 19/00
[52] U.S. Cl. ...................................... 55/210; 55/274; 55/467; 55/213; 417/42; 417/43; 96/113
[58] Field of Search ................. 55/210, 213, 274, 387, 55/467; 417/42, 43; 96/113

[56] References Cited

U.S. PATENT DOCUMENTS

| | | | |
|---|---|---|---|
| 3,518,814 | 7/1970 | Magnard | 55/210 |
| 3,811,250 | 5/1974 | Fowler | 55/473 |
| 4,257,746 | 3/1981 | Wells | 417/43 |
| 4,642,128 | 2/1987 | Solorzano | 55/467 |
| 4,786,295 | 11/1988 | Newman et al. | 55/213 |
| 4,810,269 | 3/1989 | Stackhouse | 55/274 |
| 4,963,134 | 10/1990 | Backscheider | 55/387 |
| 4,986,839 | 1/1991 | Wertz et al. | 55/274 |
| 5,047,072 | 9/1991 | Wertz et al. | 55/387 |

*Primary Examiner*—Bernard Nozick
*Attorney, Agent, or Firm*—Trask, Britt & Rossa

[57] ABSTRACT

A surgical laser smoke evacuation system includes a sensor positioned at the surgical site to determine the need for evacuation. A vacuum pump draws smoke from the site through a system of conduits, including an in line filter. The filter tends to become clogged over time. A sensor determines changes in the pressure drop across the filter, and is connected to a control mechanism which adjusts the speed of the vacuum pump to maintain an approximately constant flow across the filter.

26 Claims, 15 Drawing Sheets

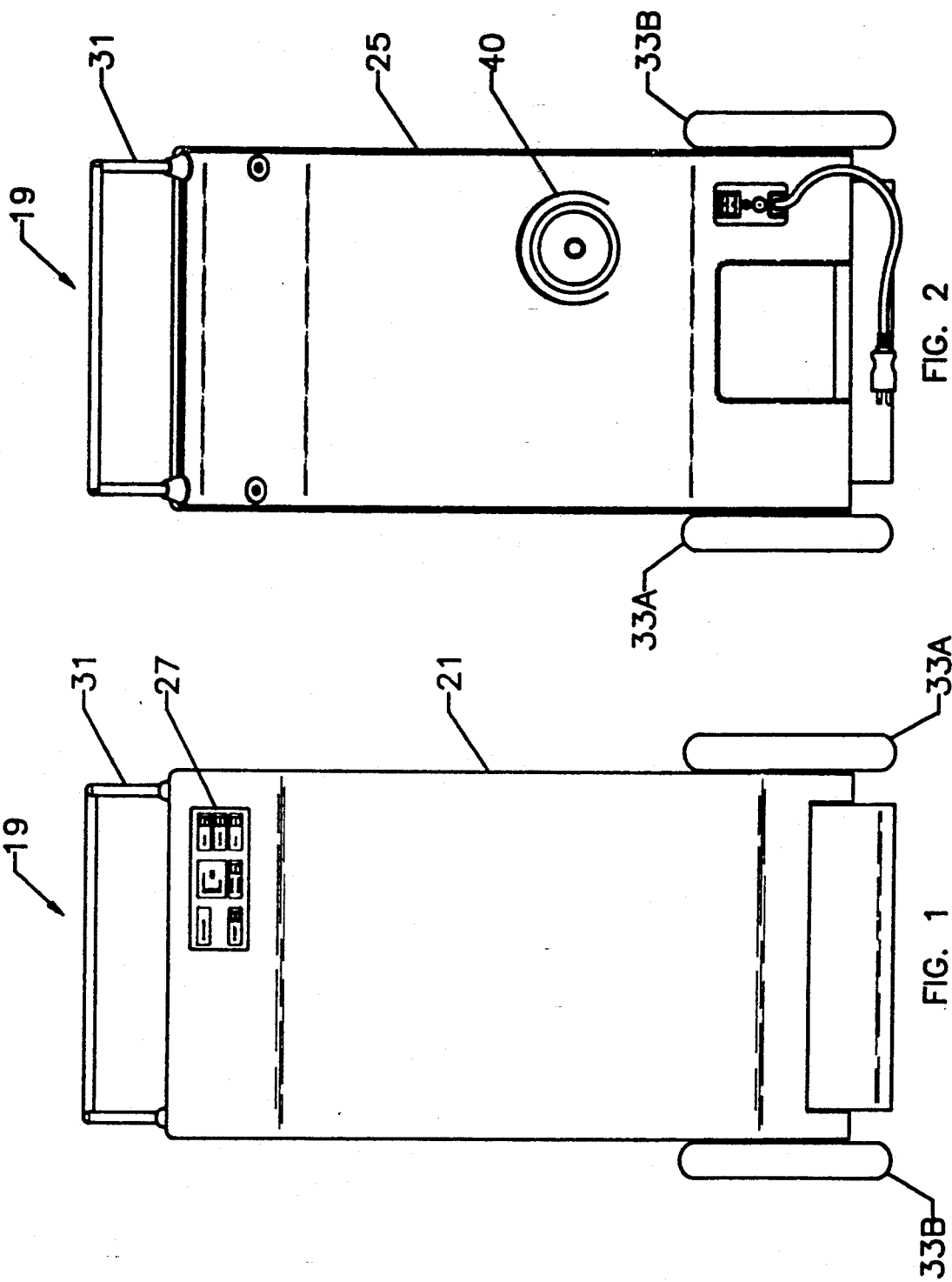

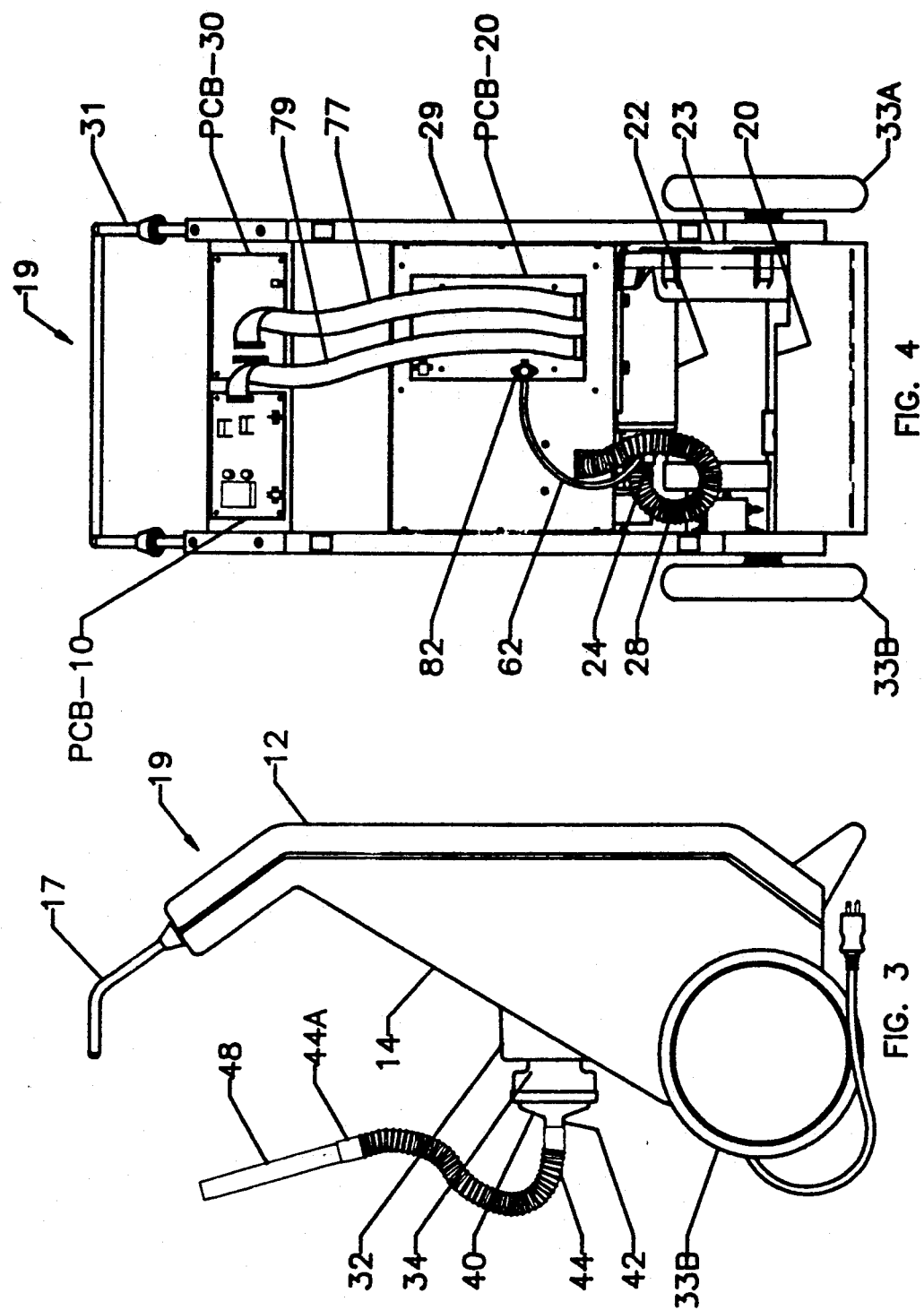

DUAL MODE LASER SMOKE EVACUATION SYSTEM WITH SEQUENTIAL FILTER MONITOR AND VACUUM COMPENSATION

This application is a continuation of application Ser. No. 07/786,455, filed Nov. 1, 1991, now abandoned.

BACKGROUND OF THE INVENTION

1. Field

This application relates to laser smoke evacuation systems used during laser surgical procedures and more specifically to laser smoke evacuation systems with smoke filter obstruction indicators.

2. State of the Art

Laser surgical procedures are widely used for removing excess or diseased tissue. When subjected to the concentrated energy of the laser, the tissue of interest is vaporized into laser smoke. The laser smoke may contain infectious viral or microbial components, and must be evacuated to prevent exposing the surgical staff to these potentially harmful components.

Devices to evacuate laser smoke generated during laser surgery typically employ a motor driven vacuum pump to suction the smoke into the device. The smoke may then be passed through a filter where particulates and potentially harmful materials are removed.

Over time, filtered material clogs the pores of the filter resulting in a change in suction capability and filtering capacity. The filter must then be replaced to maintain a safe environment for the surgical staff. If the filter becomes extensively clogged during surgery, it may be necessary to stop the surgery until the filter can be changed.

Several U.S. patents teach devices to evacuate and filter laser smoke generated during laser surgery. Some of the devices are capable of indicating a clogged filter condition. These devices, however, do not indicate the extent of filter obstruction, or compensate for a change in suction capability as the filter becomes clogged.

It would be useful to know the extent of filter obstruction at all times. A substantially clogged filter could then be replaced before beginning a surgery. It would also be useful if the smoke evacuation system could compensate for a change in suction capability as the filter progressively becomes clogged. Ideally, such a system should be capable of automatically controlling the level of evacuation to correspond with the level of laser smoke production.

SUMMARY OF THE INVENTION

A laser smoke evacuation system includes a motor driven vacuum pump and means, such as a filter, for removing harmful components from laser smoke. A filter status response means may be included for monitoring and reacting to the porosity condition of the filter. Porosity condition may be indicated to an operator by an indicator means. In such embodiments, the indicator means may be made to sequentially indicate the porosity condition as the filter becomes progressively less porous due to clogging. A control panel may be included for mounting and displaying various switches and indicators of the smoke evacuation system. In such embodiments, indicator lights sequentially light as the filter becomes progressively more clogged.

Certain embodiments of the invention automatically compensate for changes in suction capability due to progressive clogging of the filter. Suction sensor means may be included to sense and respond to changes in suction capability. In such embodiments, the suction sensor means may be associated with the motor to cause motor speed, and thus vacuum pump speed to change in response to a signal from the suction sensor means. Typically, a pressure sensor associated with the vacuum pump senses changes in negative pressure as the filter becomes clogged, and produces an output signal which corresponds to the negative pressure produced by the pump. The pressure sensor output signal is amplified and applied to an electrical circuit associated with the motor. The output from this circuit increases or decreases the pump speed to maintain a constant level of suction.

Certain embodiments of the invention are operable in either of two modes. In an internal mode, the vacuum pump speed may be selected from a plurality of preselected speeds. Switches corresponding to preselected pump speeds may be located on the front panel for convenience. In an external mode, vacuum pump speed may be automatically determined in response to an output signal from a sensor element linked to the system. The sensor element may be linked to an electronic circuit which controls the speed of the vacuum pump. In the preferred embodiments, the sensor element generates an output signal corresponding to the level of laser smoke production, thereby regulating pump speed proportional to the need for suction at the operative site.

BRIEF DESCRIPTION OF THE DRAWINGS

In the drawings, which illustrate what is currently regarded as the best mode for carrying out the invention:

FIG. 1 is a front elevation view of the laser smoke evacuation system of the instant invention;

FIG. 2 is a rear elevation view of the laser smoke evacuation system of FIG. 1;

FIG. 3 is a side elevation view of the laser smoke evacuation system of FIG. 1;

FIG. 4 is a front elevation view of the laser smoke evacuation system of FIG. 1 with the housing removed to show the components inside.

DETAILED DESCRIPTION OF THE ILLUSTRATED EMBODIMENT

Figure 6:
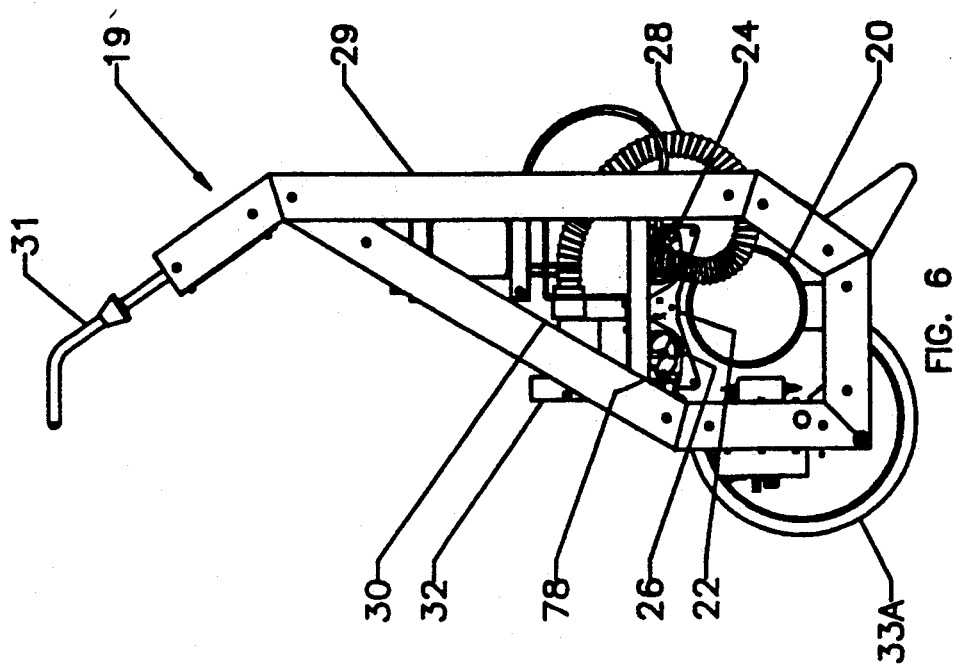
FIG. 6 is a side elevation view of the laser smoke evacuation system of FIG. 1 with the housing removed.
Figure 5:
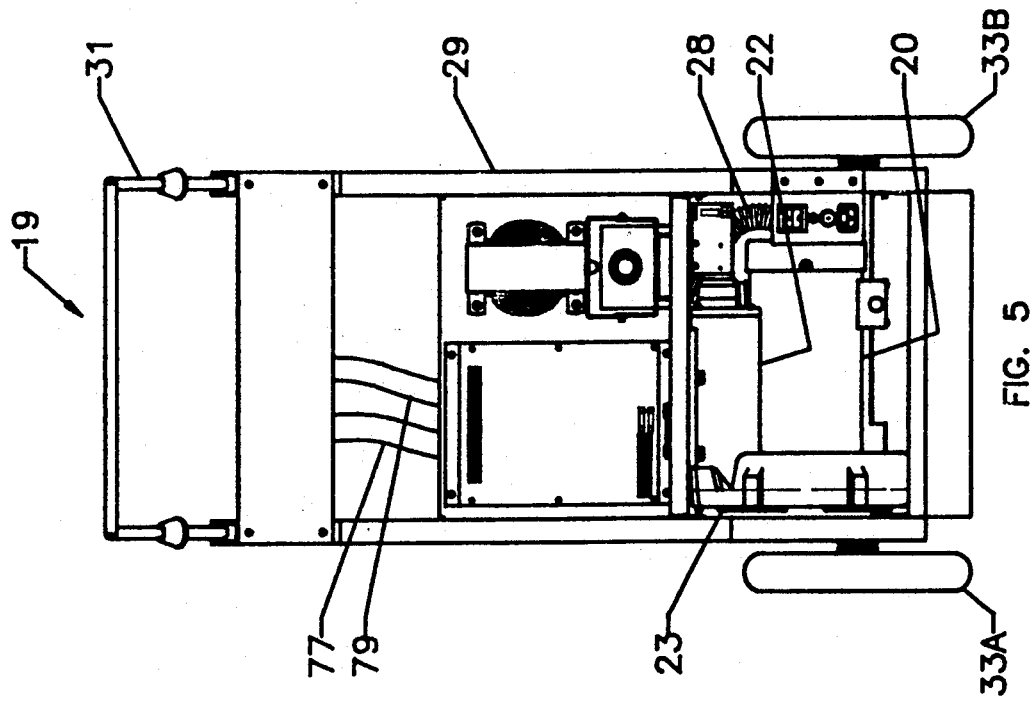
FIG. 5 is a rear elevation view of the laser smoke evacuation system of FIG. 1 with the housing removed.

Referring to FIGS. 1-3, the laser smoke evacuation system 19 may include a front housing panel 21 and a rear housing panel 25 to shield and protect internal components within the housing panels. A control panel 27 may be mounted to a housing panel as illustrated so that it is readily accessible to an operator. Referring also to FIGS. 4-6, a frame 29 is structured so that the internal components of the system may be mounted thereto. A handle 31 facilitates tilting of the evacuation system onto the wheels 33A and 33B for transport of the system.

An electric motor 20 is mechanically connected to a vacuum pump 22 by a connection means 23 such as a gear box, or belt drive arrangement. Electric motor 20 mechanically operates pump 22 causing air to be transported from a pump inlet 24 to a pump outlet 26 thereby creating a negative pressure at the pump inlet 24. A first suction duct 28 connects pump inlet 24 to the receiver outlet 30 of a filter receiver 32.

As best shown by FIG. 3, a filter 40 is mounted to the receiver inlet 34 of filter receiver 32. Inlet 34 is structured to allow filter 40 to be removed and replaced as required. Filter 40 may be a conventional single or multistage filter, or it may be designed according to the requirements of a particular application. Filter 40 has an inlet 42 adapted for connection to a second suction duct 44. The second suction duct 44 is of sufficient length to extend from filter inlet 42 to a point proximal the surgical site. A fluid pathway exists from the surgical site, through the second suction duct 44, filter 40, filter receiver 32, and first suction duct 28 to the negative pressure at pump inlet 24. Laser smoke produced during laser surgery may be suctioned into the second suction duct 44 and through filter 40 where particulate matter and potentially harmful components are removed.

The first and second suction ducts 28 and 44 may be constructed from a flexible material such as plastic, fabric or elastomeric material. In a preferred arrangement, first and second suction ducts 28 and 44 are constructed from flexible convoluted tubing. The distal end 44A of the second suction duct 44 may be structured to accommodate installation of a sterilizable nozzle 48 to ensure sterility at the surgical site.

In practice, laser smoke is removed from the atmosphere surrounding an operating area in which the smoke is created. The evacuation system 19 is wheeled into the operating area and motor 20 is connected to a source of power and is turned on. The motor 20 drives the vacuum pump 22.

Pump 22 pulls the ambient air, with the smoke, through a nozzle 48, which has been placed in the area from which smoke is to be removed, duct 44 to which the nozzle is connected, filter 40, filter receiver 32, duct 28, and pump inlet 24 and then discharges the filtered air to atmosphere through the pump outlet 26.

The pump 22, motor 20 and filter receiver 32 are each mounted to the frame 29 and pump 22 and motor 20 are internal of the front housing panel 21 and the rear housing panel 25. Filter receiver 32 projects through the rear housing panel, and mounts the filter 40.

Figure 7:
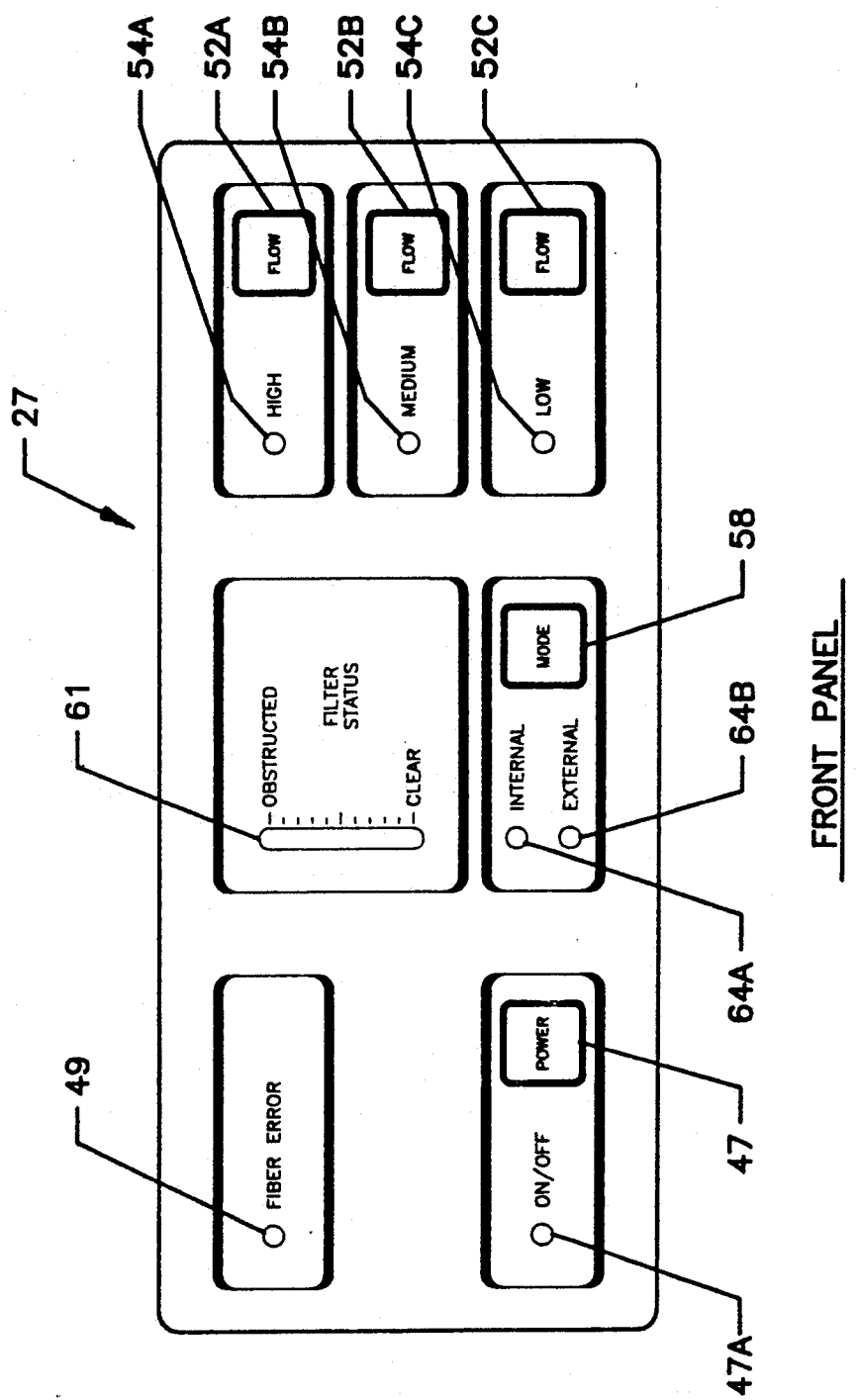
FIG. 7 is front elevation view of one embodiment of the front panel.

Referring to FIGS. 1 and 7, a control panel, indicated generally as 27, may be included on front housing panel 21 to display the status or condition of various components of the smoke evacuation system. Switches and indicators pertaining to operation of the smoke evacuation system, such as power switch 47 and indicator light 47A, may be mounted on control panel 27. The panel 27 provides a convenient and accessible location to consolidate various switches and indicators which may be included with the smoke evacuation system. It is desirable that indicator lights be of the LED variety for reliability and compatibility with other electronic components of the system.

Electric motor 20 may be of conventional design and appropriately sized to drive vacuum pump 22. In a preferred arrangement, motor 20 may be operated at different speeds. Multi-speed capability may be accomplished by either operating the motor 20 at any of a plurality of preselected motor speeds or through operation in a duty cycle. If a different level of evacuation is desired, the speed of the motor, and hence the speed of the vacuum pump, may be changed to any of the preselected speed settings. Motor speed may be changed by pressing a button, such as one of buttons 52A, 52B, or 52C on the front panel 21, which corresponds to the desired level of evacuation. The appropriate speed indicating light, such as one of indicating lights 54A, 54B, or 54C, will light to indicate the selected motor speed.

Figure 8:
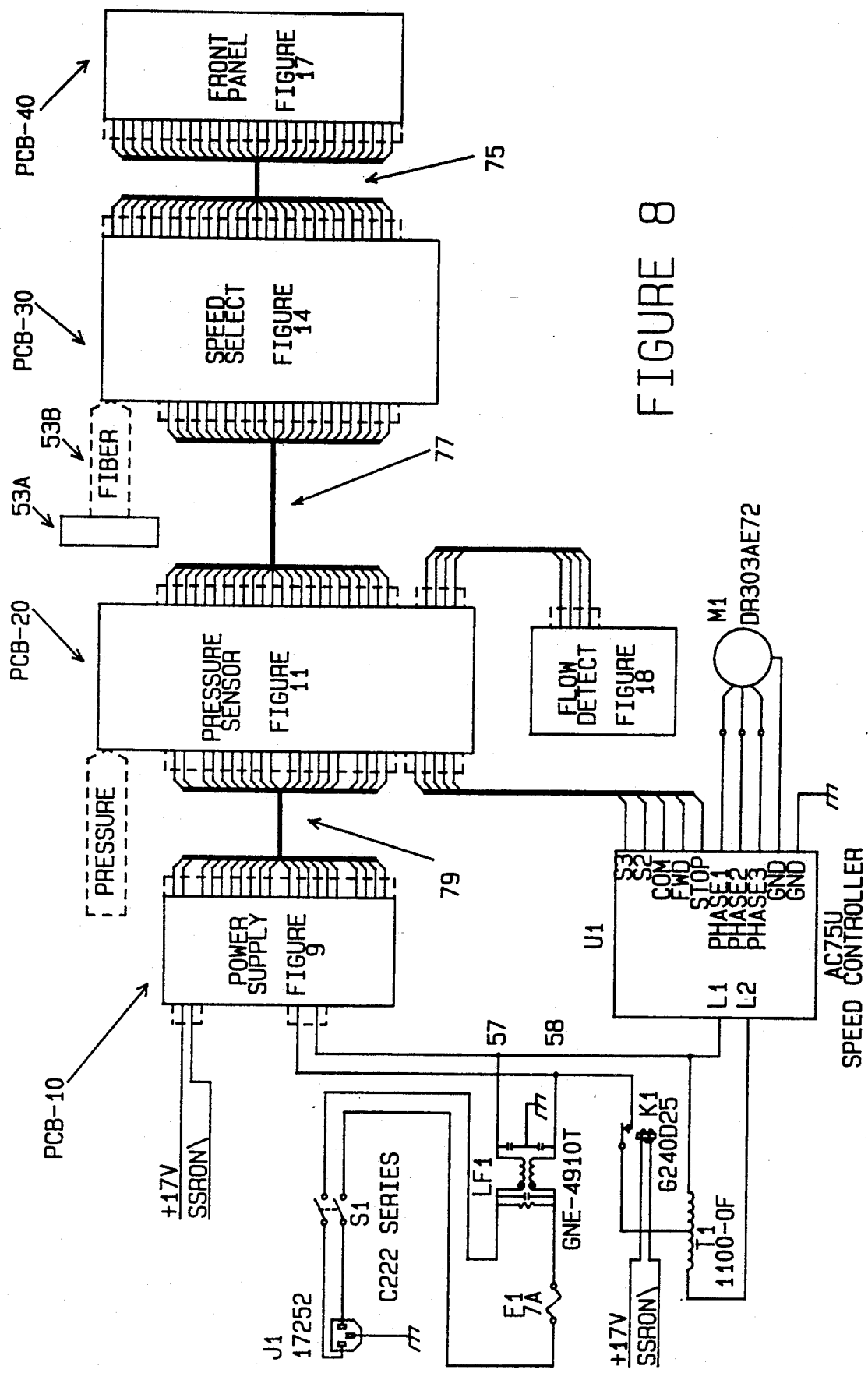
FIG. 8 is a schematic circuit diagram of the electronic system of the laser smoke evacuation system of this invention.

FIG. 8 is a schematic diagram of a practical electrical circuit for the electronic system of the smoke evacuation system, showing the various printed circuit boards which may be included; namely a power supply board, PCB-10, a pressure board, PCB-20, a speed select board, PCB-30 and a control board PCB-40. FIGS. 9-18 are schematic diagrams of practical electrical circuits of the printed circuit boards and other electronic components which may be included in the electronic system. Wherever possible, practical values or manufacturers identification numbers for the illustrated electrical components are included. Pin position and other electronic details are indicated on the drawings in conventional fashion.

Referring to FIG. 8, when switch S1 shown at the left side of the figure is closed, power from an AC source (not shown) is supplied through an outlet J1 to the system through fuse F1 and line filter LF1. The line filter LF1 may be included to prevent transient interference voltages from entering or leaving the system. The high side 56 of the AC line exiting line filter LF1 is applied to solid state relay K1 and to the power supply printed circuit board PCB-10 as indicted by the signal AC HI. The low side 57 of the AC line is applied to one side of auto-transformer T1, terminal L1 of AC75U speed controller U1, and to the power supply printed circuit board PCB-10 as indicated by the signal AC LO.

Figure 9:
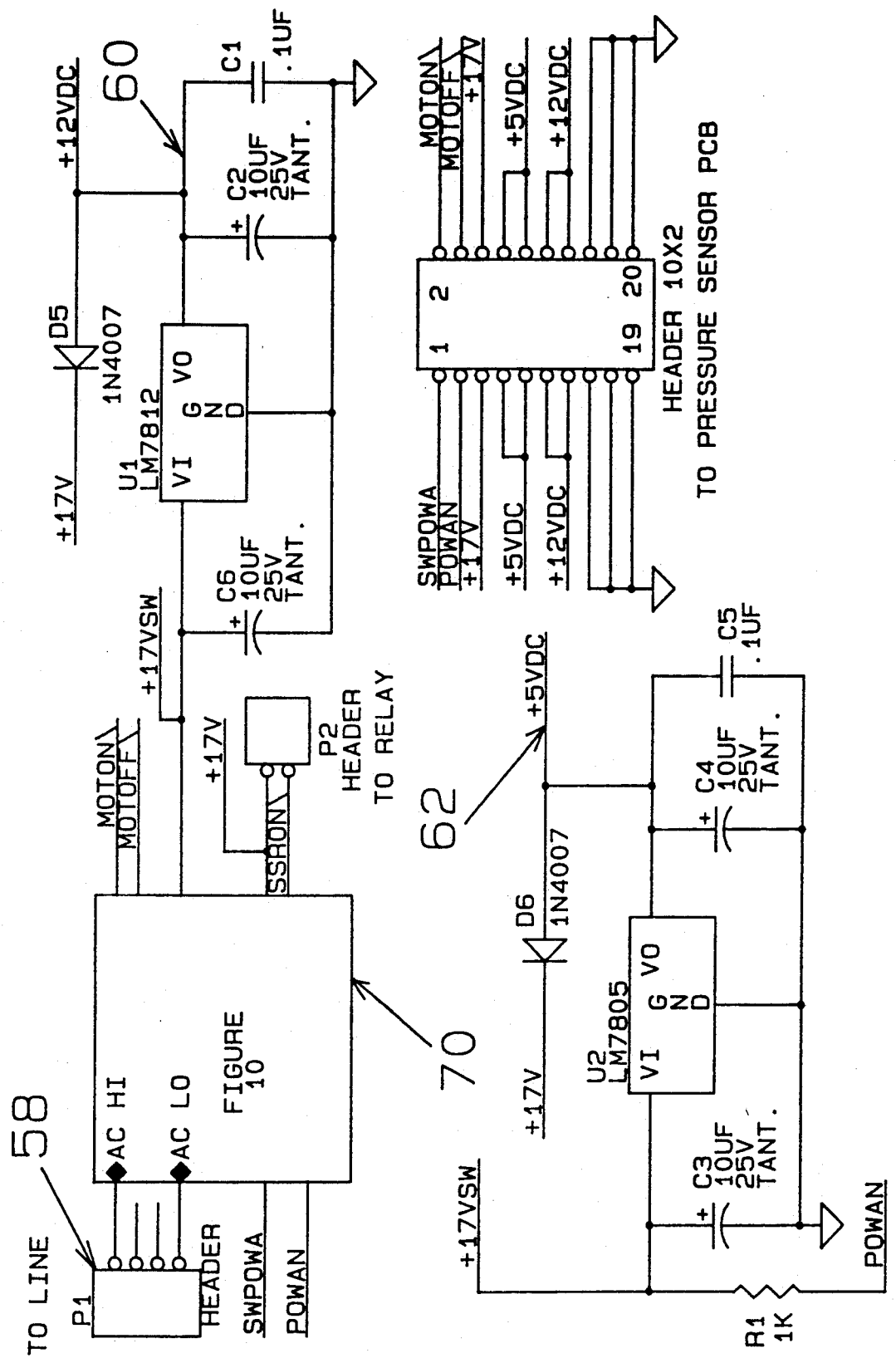
FIG. 9 is a schematic circuit diagram of a portion of the power supply printed circuit board of the electronic system of FIG. 8.
Figure 10:
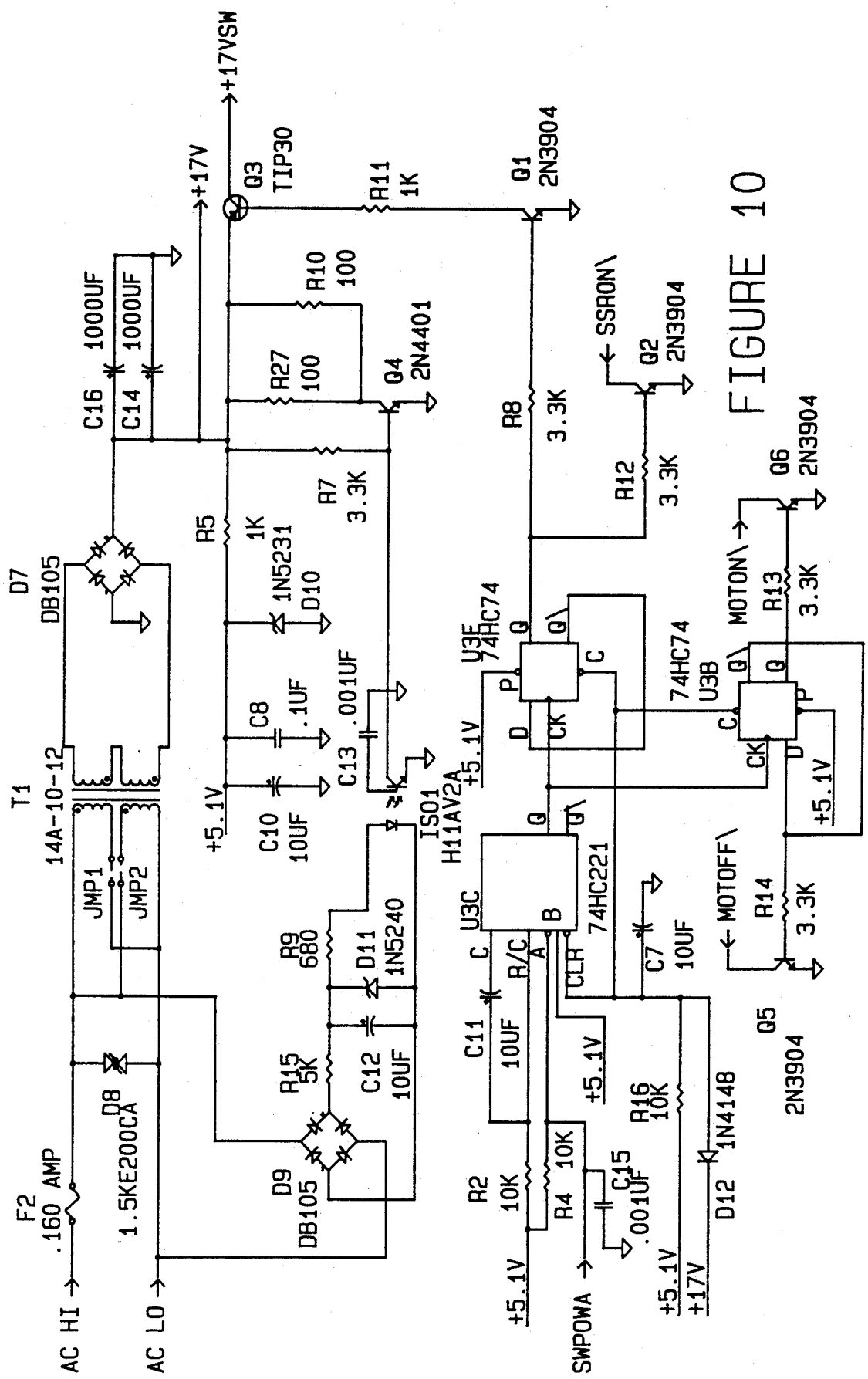
FIG. 10 is a schematic circuit diagram of another portion of the power supply printed circuit board.
Figure 11:
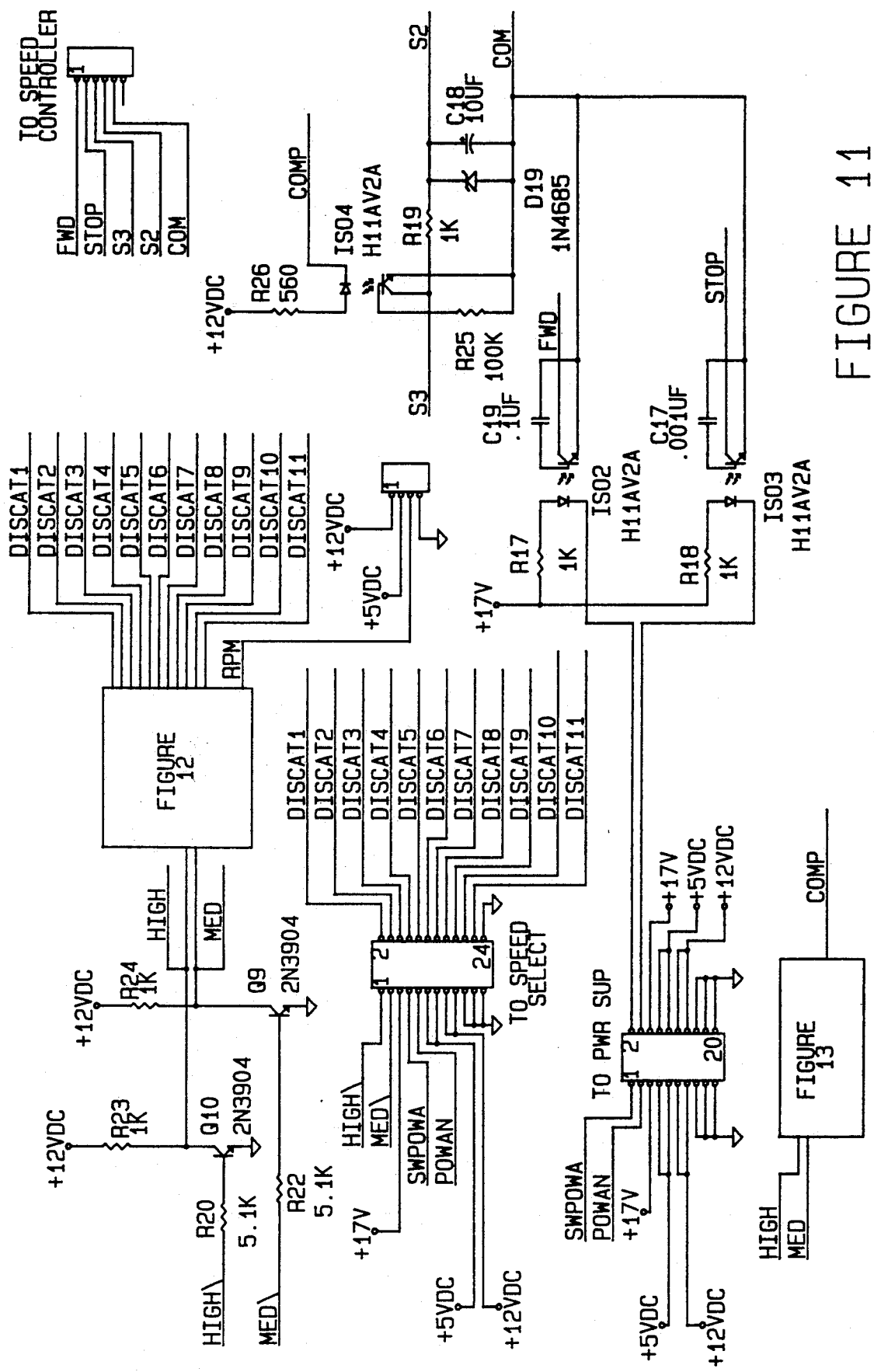
FIG. 11 is a schematic circuit diagram of a portion of the pressure sensor printed circuit board of the electronic system of FIG. 8.

As shown in FIG. 9, the AC HI and AC LO electrical signals (FIG. 8) are applied to the power supply portion 70 of the power supply printed circuit board PCB-10 at pin P1 on header 58. FIG. 10 is a schematic diagram of the power supply portion 70 of FIG. 9. The electrical signal indicated by signals AC HI and AC LO are processed by the circuit illustrated, which delivers a rectified and smoothed positive 17 Volt potential at an output indicated at the right side of FIG. 10 as +17VSW Referring again to FIG. 9, the potential +17VSW exiting the power supply portion 70, is in turn applied to various other components illustrated in FIG. 9, notably the voltage regulators U1 and U2. The +17 Volt potential into a +12 Volt component 60, and a +5 Volt component 62. As shown in FIG. 8, it is these potentials which exit the power supply printed circuit board PCB-10 to supply power to the rest of the electronics within the system.

Figure 16:
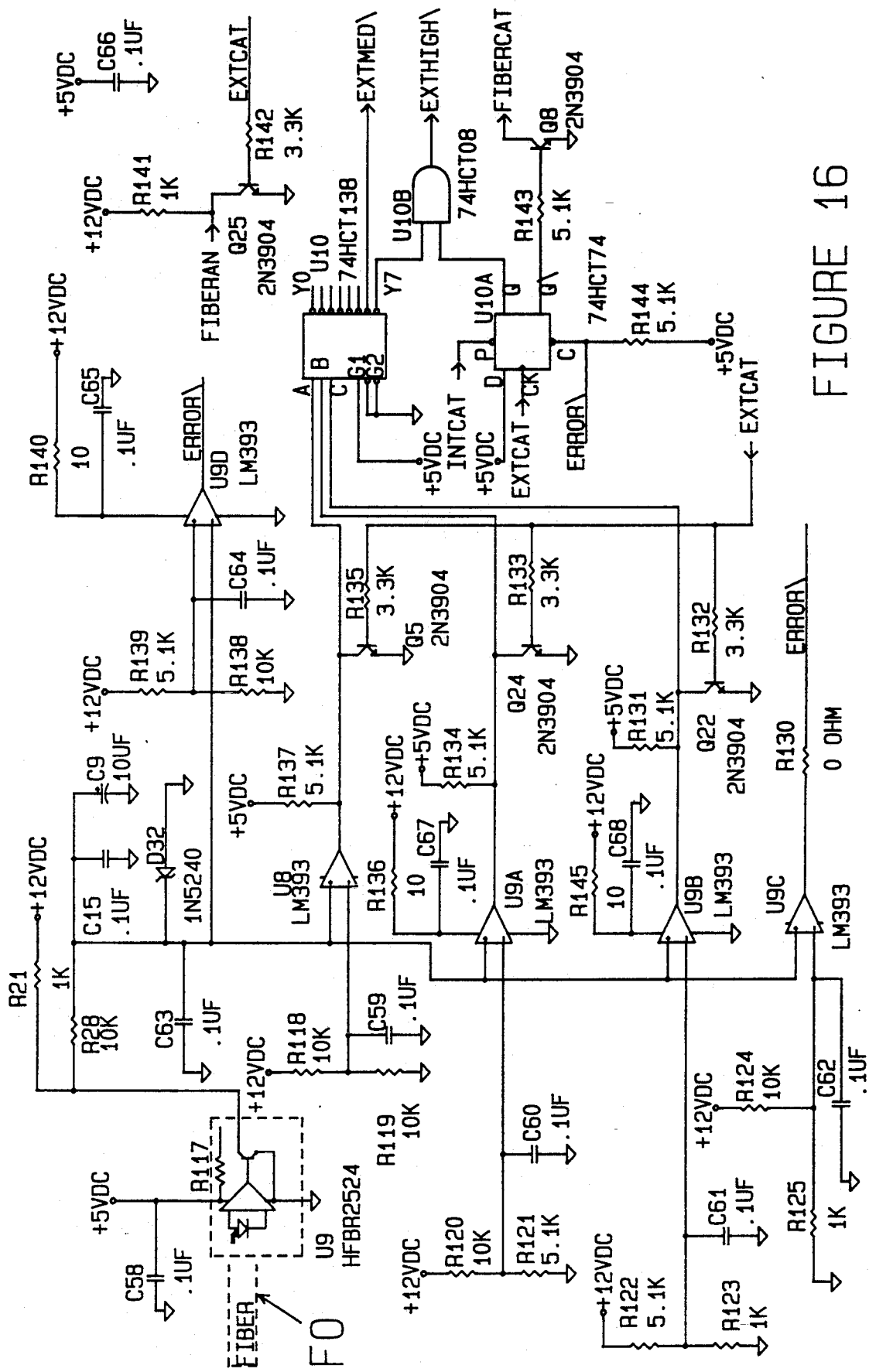
FIG. 16 is a schematic circuit diagram of another portion of the speed select printed circuit board of FIG. 8.
Figure 17:
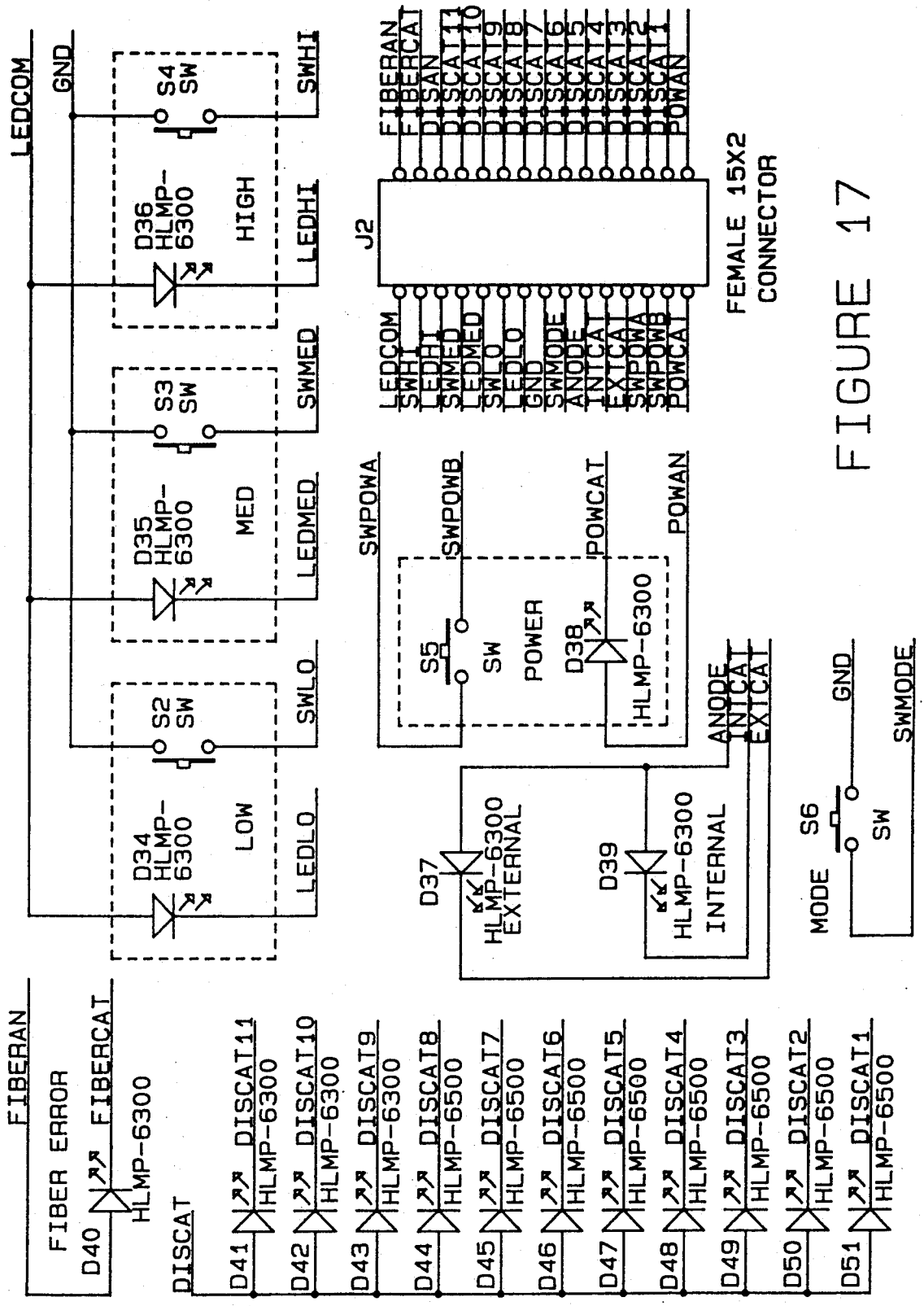
FIG. 17 is a schematic circuit diagram of the control panel electronic components of the electrical system of FIG. 8.

A practical circuit for the electronics of the control panel 27 is shown schematically by FIG. 17. Switch S5 (power), is connected to AC female 15×2 connector J2, the connection of which provides electrical signals SWPOWA and SWPOWB. These electrical signals are fed from the control panel printed circuit board PCB-40, through a ribbon cable indicated generally as 75 (FIG. 8), to the speed select printed circuit board PCB-30. FIG. 14 shows a portion of the speed select printed circuit board PCB-30 and shows electrical signal SWPOWB connected to ground and signal SWPOWA entering the circuit board at 15×2 Header P1 at pin number 25. Electrical signal SWPOWA exits the circuit board at 12×2 Header P2 at pin number 7. The signal SWPOWA leaves the speed select printed circuit board PCB-30 through a ribbon cable indicated generally as 77 (FIG. 8) and enters the pressure sensor printed circuit board PCB-20. In like manner, the other electrical signals indicated on the printed circuit boards PCB-10 through PCB-40 in FIG. 8, enter and exit the printed circuit boards as indicated in FIGS. 9–18.

Figure 14:
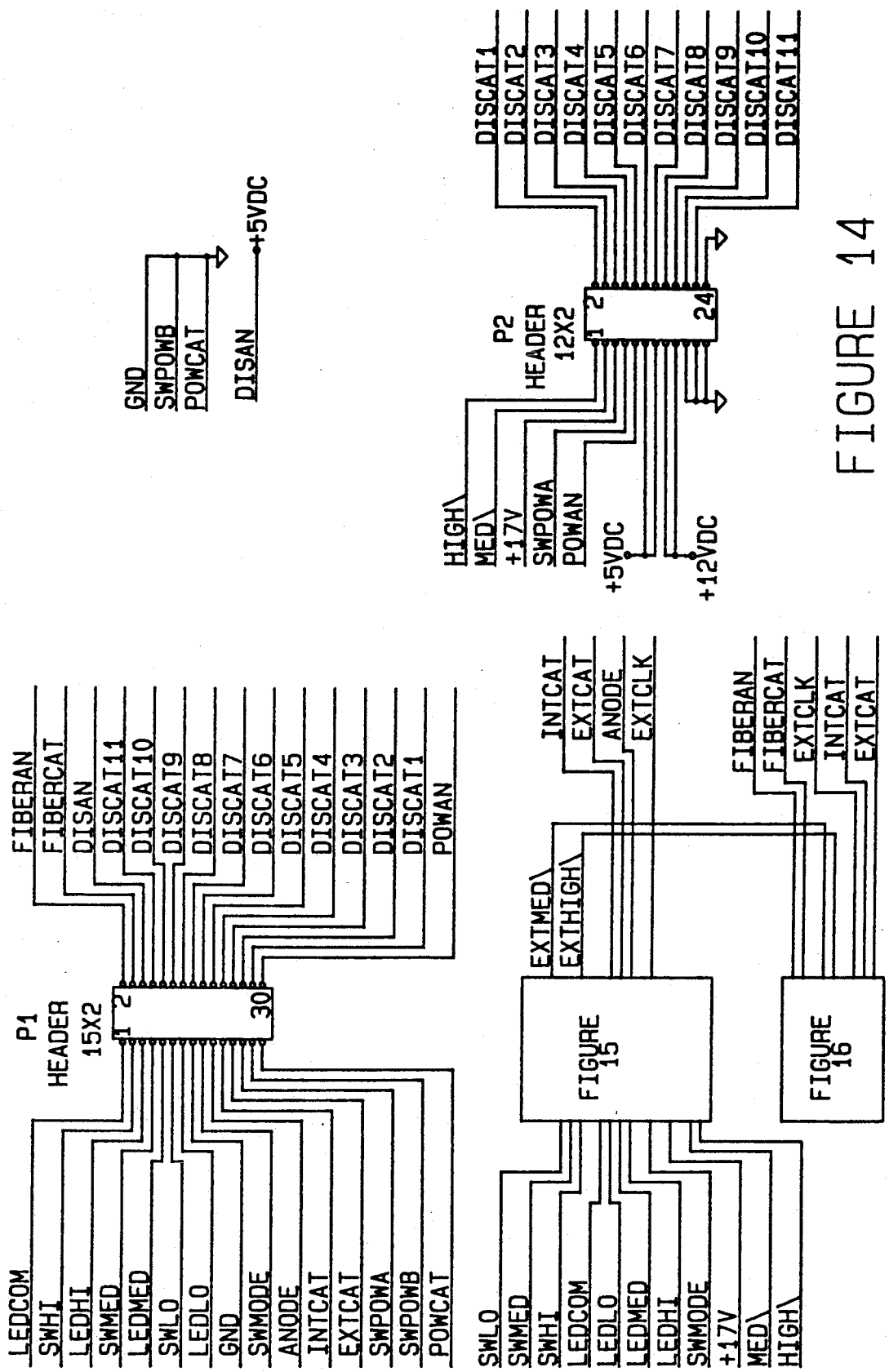
FIG. 14 is a schematic circuit diagram of a portion of the speed select printed circuit board of the electronic system of FIG. 8.
Figure 15:
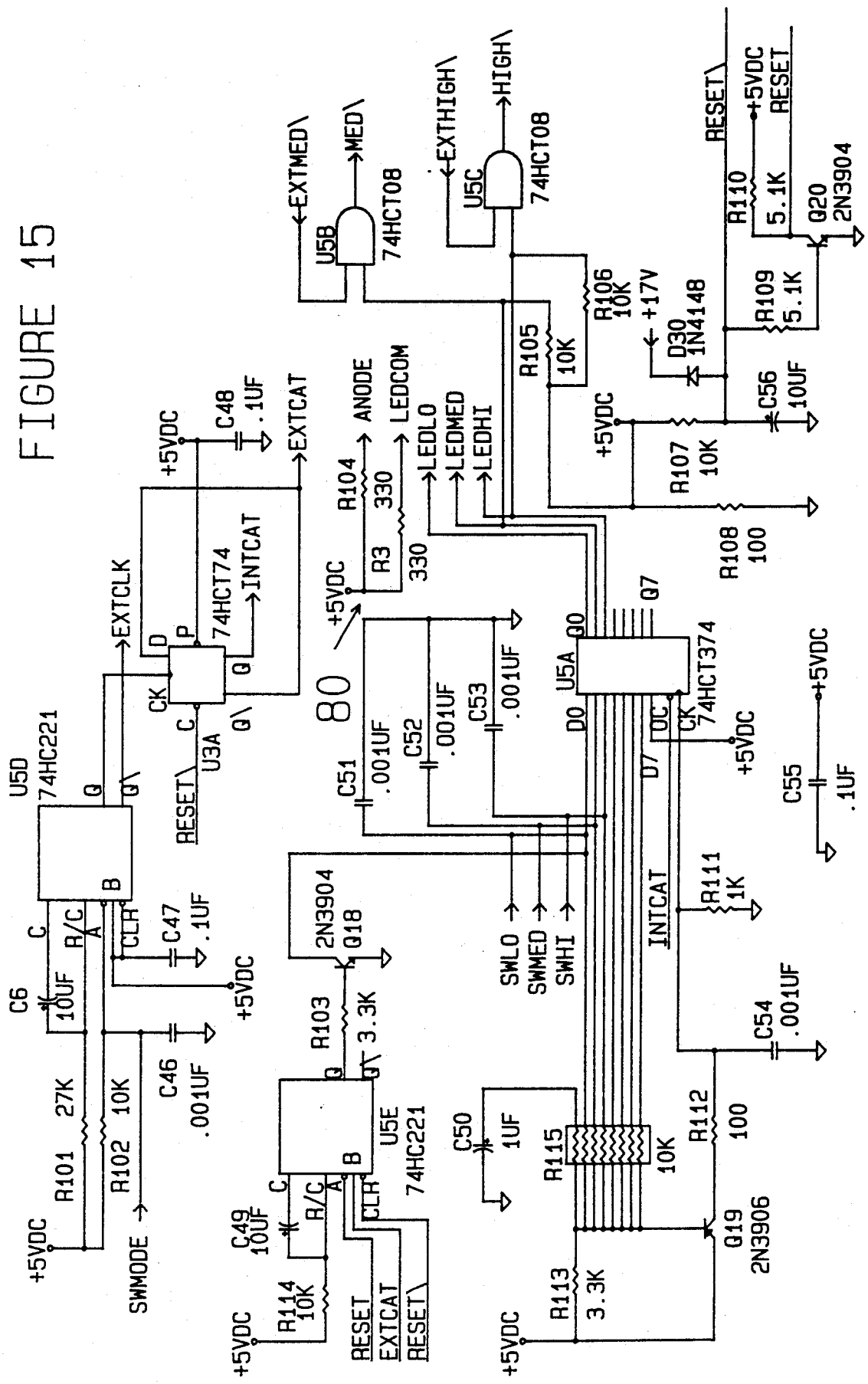
FIG. 15 is a schematic circuit diagram of another portion of the speed select printed circuit board of FIG. 8.

The speed select printed circuit board PCB-30 is shown schematically in FIGS. 14, 15, and 16. The circuit board is typically designed to cause default to the lowest motor speed when the smoke evacuation system is turned on. FIG. 17 shows three speed selection switches S2, S3, and S4. One side of each of these switches is connected to ground, and the other side of each switch attaches to an input of an octal latch U5A as shown in FIG. 15. If a speed other than the default low speed is selected from the control panel, the switch is shorted and the input at octal latch U5A is pulled to a low voltage state. The low voltage input is transferred to the appropriate output pin of octal latch U5A where it latches the signal on the low voltage output. U5A output signals are fed to AND gates U5B and U5C and also to the appropriate LED on panel 27. FIG. 17 shows the LED connections as electrical signals LEDLO, LEDMED, and LEDHI from female connector J2 and going to the cathodes of diodes D34, D35, or D36. If the medium speed were selected, the electrical signal LEDMED would go to a low voltage state and the LED representing the medium speed (54B, FIG. 7) would lite up. Current flows from the direct current source so, through resistor R3 electrical signal LEDCOM to the appropriate anode of a diode D35 in the control panel circuitry (FIG. 17), and back to the low voltage output of octal latch U5A.

In a preferred arrangement, electric motor 20 is operable in either of two modes. In an internal mode, the operator may select the motor speed from a plurality of switches 52A, 52B, and 52C on the control panel 27 corresponding to a plurality of preselected motor speeds. In an external mode, the motor is coupled to a sensor element 53A by means of a fiber optic cable 53B. The motor speed, and thus the available suction, is then controlled in response to an output signal from the sensor element. The sensor element may be positioned proximal the surgical site where it is in close proximity to the laser smoke. The fiber optic cable conducts a light signal from the sensor element to an electronic circuit which converts the light signal to an electrical signal. The electrical signal is converted from the light signal on the speed select printed circuit board PCB-30 which controls the motor speed in response to the signal from the sensor element.

The external mode ensures an adequate level of evacuation for the level of laser smoke generation. As the amount of smoke changes, the output from the sensor element also changes, and the level of evacuation is adjusted in response. Selection of internal and external modes may be accomplished by actuating a switch 58 located on the control panel 27. Indicator lights 64A and 64B may be used to indicate which of the two operational modes has been selected Indicator lights 54A, 54B, and 54C may be used to indicate which of the preselected motor speeds has been selected. As specifically illustrated, they do so only in the internal mode.

The speed select printed circuit board PCB-30 controls mode selection as shown by FIGS. 15 and 16. The circuit may be designed to default to the internal operational mode when the evacuation system is turned on. In this arrangement, when power switch 47 is actuated, the electrical circuit for the internal mode is enabled and power is routed to the internal LED indicator 64A on control panel 27. When the mode button 58 is pressed to change to external mode, a low voltage signal, SWMODE (FIG. 17), is fed to a one-shot multivibrator U5D (FIG. 15). Low voltage signal SWMODE triggers an output signal, EXTCLK (FIG. 16), which is sent to dual D flip-flop U3A. In response to output signal EXTCLK, U3A produces a high voltage signal, INTCAT, which disables the LOW, MED, and HI control panel switches 52A, 52B, and 52C from interfering with the speed of the vacuum motor. High voltage signal INTCAT also enables flip-flop U3A and turns off the internal LED 64A on the control panel 27. A low voltage signal from dual D flip-flop U3A, EXTCAT (FIG. 15), is fed to the external LED 64B on control panel 27 to illuminate the LED as an indicator that the system is in the external mode. These actions set the system for external speed control. If the mode button 58 is pressed again, the internal LED 64A comes on, the external LED 64B goes off, and the system is returned to internal mode at the lowest speed.

In the external mode, the vacuum motor 20 speed, and thus the available suction, is controlled in response to an output signal from a sensor element (not shown). The intensity of the output signal corresponds to the level of laser smoke production at the surgical site. As shown in FIG. 16, the external device is coupled to the vacuum unit by a fiber optic cable (not shown), the input of which is indicated as FO. The fiber optic cable conducts a light signal from the sensor element to the speed control printed circuit board PCB-30. The light signal is converted back into an electrical signal within the evacuation system by a fiber optic detector U9. When light is present in the fiber optic cable, the output of detector U9 is pulled to a low voltage through an internal U9 transistor. Current thus flows from the source +12VDC, through resistor R21 to ground. When light is not present in the fiber optic cable, the internal output transistor of U9 is off and currant flows from +12VDC through R21 and R28, and charges C9 and C15. When the light signal again turns on, the output transistor of U9 turns on, and current not only flows through resistor R21 to ground but also from C9 and C15, through R28, to ground which discharges the capacitors. The ratio of charge time to discharge time determines the average voltage level across capacitors C9 and C15, which in turn determines the speed of the motor 20. If the capacitor voltage is 5 volts for example, comparators U9A, U9B, U9C, and U9D will be in a high voltage state. The output of comparator U8 will be at a low voltage. The output potentials of comparators U8, U9A, and U9B are fed to input terminals A, B, and C of decoder U10. One output Y0–Y7 of decoder U10 provides a low voltage signal depending upon the binary input combination from the comparators. In the case illustrated, the binary inputs cause the output Y6 to achieve a low voltage state because the B (weighted value of 2) and the C (weighted value of 4) inputs are at high voltage. The output Y6 signal EXTMED, causes the vacuum motor 20 to run at a medium speed when the signal is in a low voltage state. The signal from the sensor element thus varies the ratio of charge time to discharge time of capacitors C9 and C15 which in turn determines the speed of the motor 20. In this embodiment, motor speed is regulated by a duty cycle when the evacuation system is operated in the external mode.

If the voltage level across capacitors C9 and C15 becomes too high or too low, an error signal may be produced. This might occur if the fiber optic cable is disconnected or damaged, or if the external control circuit fails. An error condition will cause the output signal of either comparitor U9D or U9C shown in FIG. 16 to go to a low voltage state. This action activates the clear input signal of flip-flop U10A and causes the output, indicated in FIG. 16 as Q, to go to a low voltage state and the output, designated as Q , to go to a high voltage state. The Q output forces the output signal indicated as EXTHIGH of AND gate U10B to go to a low voltage state which causes the motor to go to high speed. The output signal of U10A, designated Q , turns on transistor Q8 which turns on the fiber error LED 49 on control panel 27. The function of this circuitry in an error condition is to drive the vacuum motor 20 at high speed to ensure adequate suction. In the internal mode, the current which might normally flow to the fiber error LED 49 is shunted to ground.

Figure 18:
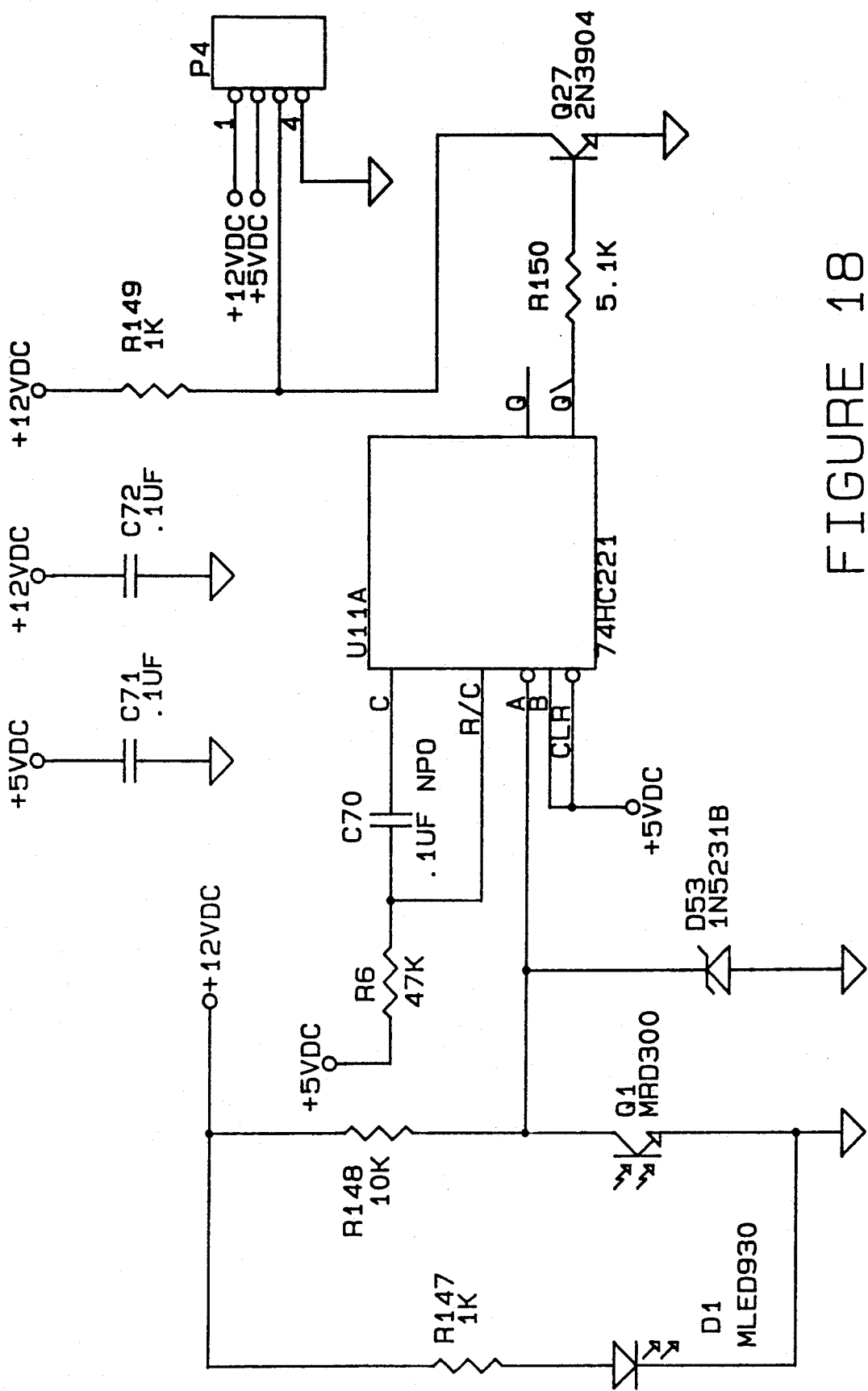
FIG. 18 is a schematic circuit diagram of the flow detector printed circuit board of the electronic system of FIG. 8.

A filter status indicator means enables a user to determine the functional condition of the filter 40. As the filter 40 becomes clogged, resistance to air-flow through the vacuum pump 22 increases, and consequently air-flow decreases. A flow detector 78 may be placed within the flow to detect a decrease in air-flow. The flow detector may include a small propeller positioned to rotate in the air-flow. As the flow changes, the speed of the propeller also changes. The propeller may be positioned so that the blades pass between an infrared LED emitter (FIG. 18, D1) and a photo-transistor detector. Each time the blade passes between the emitter (D1, FIG. 18) and detector (Q1, FIG. 18), the light beam is interrupted and the photo-transistor changes from on to off. As the speed of the propeller changes, the frequency of light beam interruption also changes. The collector of detector Q1 may be selected to provide a square wave output profile with frequency representing the speed of the propeller. This output wave may be fed to the input of a one-shot multivibrator formed by dual one-shot multivibrator U11A and other associated components (FIG. 18). When the input of U11A receives a negative going edge, a one-shot output is triggered to low voltage for a period defined by the resistor/capacitor network of R6 and C70. The result is a square wave output signal which varies in frequency and duty cycle. This wave can be applied to a resistor/capacitor filter to obtain a varying DC voltage representing the frequency of the propeller, and consequently the air-flow.

If the pump speed is varied, air-flow also varies, and the output from the resistor/capacitor filter will change. To maintain a uniform output, whether the pump is set to LOW, MED or HIGH speeds, the gain and offset of the inverting amplifier receiving the output must change with the speed of the pump. The gain variation is accomplished by the analog switches U6A and U6B shown in FIG. 12. For example, if high speed is selected, resistors R58, R60 and R57, R59 are shunted by analog switch U6B. Gain is then determined by the ratio between resistors R56, R62, and R61. For example, high gain can be adjusted by turning R62 until the appropriate output voltage from inverting amplifier U7A is obtained. Similar adjustments may be performed for other speed selections.

If the offset is set when the pump is running at high speed, and then the speed is changed, a different offset is applied to inverting amplifier U7A due to the action of the analog switches. Referring again to FIG. 12, when high speed is selected, analog switch U6D is turned on by the signal HIGH, resistors R71 and R70 are shunted, and the offset is adjusted by turning resistor R72. Offsets at other motor speed settings may be adjusted similarly. It is important to adjust the offsets in the order of high speed to low speed because the medium offset will affect the low offset, and the high offset will affect the other two offsets.

Figure 12:
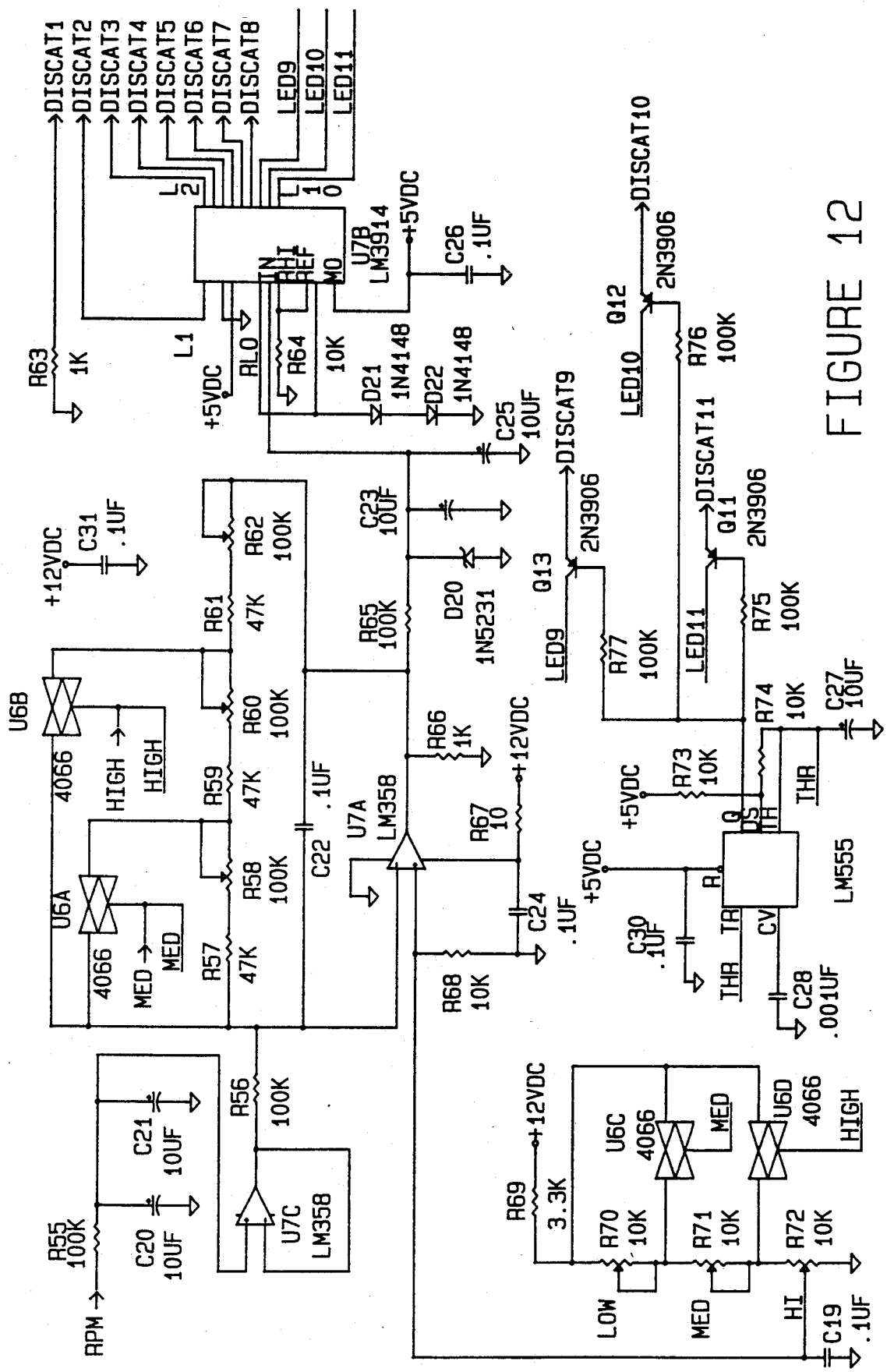
FIG. 12 is a schematic circuit diagram of a separate portion of the pressure sensor printed circuit board of FIG. 8.

As shown in FIG. 12, the output of dual op-amp U7A may be fed to the input of display driver U7B. The display driver U7B compares the incoming signal internally to a series of 10 reference voltages, within U7B, each controlling an output designated as L1–L10. If a reference is exceeded, its corresponding output goes to a low voltage state. As the input signal climbs in intensity, it exceeds an increasing number of reference voltages which sequentially allow additional output potentials to go to a low voltage state. These low voltage outputs may be coupled to the filter status LED's 61 located on control panel 27. When the outputs go to low voltage, a shunt is tripped and the LED turns on. The series of LED's 61 on the control panel 27 may resemble a bar graph which displays filter status. The first LED's to light may be colored green to indicate favorable or clear filter status, while the last LED's to light may be colored red indicating that the filter is clogged and should be replaced. To further emphasize the clogged filter condition, the red LED's may be made to flash on and off.

The system also provides for automatic compensation of suction capability as the filter becomes progressively clogged. The circuit functions by regulating the negative pressure of the vacuum pump 22 at the pump inlet 24 side. Air-flow through the vacuum pump 22 will remain constant provided the resistance to flow remains the same. If a filter is attached to the input, the resistance to flow increases, and consequently the air-flow will decrease.

Figure 13:
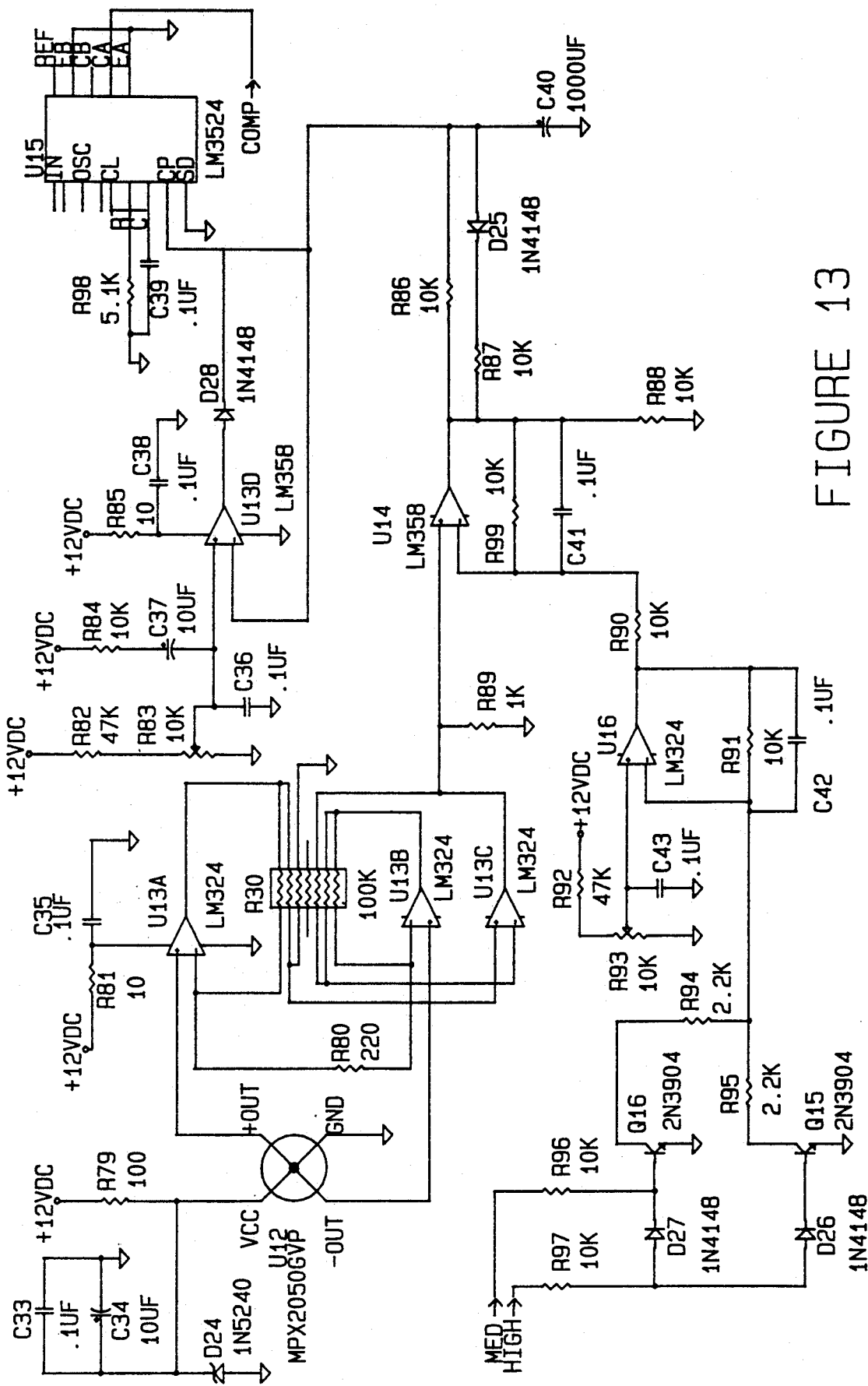
FIG. 13 is a schematic circuit diagram of another portion of the pressure sensor circuit board of FIG. 8.

This discrepancy is alleviated by the circuit illustrated by FIG. 13. A differential voltage output from a pressure sensor U12 is amplified by an instrumentation amplifier formed by the operational amplifiers U13A, U13B, and U133C, and resistor network R30. Referring to FIG. 4, a pressure sensor 82 may be coupled to the vacuum pump 22 between the pump inlet 24 and any attachments such as the filter 40 by a small hose 62. An increase in pressure is sensed by pressure sensor U12 which produces an output signal in the form of a differential voltage that increases in amplitude as the negative pressure increases. The instrumentation amplifier of U13A, U13B, U13C and resistor network R30 feeds the output to the input of a non-inverting, or error amplifier formed by dual op-amp U14 and associated components illustrated by FIG. 13. The output of U14 is applied to the input of the pulse width modulator U15, which subsequently produces a square wave output signal which has a variable duty cycle based on the amplitude of the input signal. As the input signal increases, the duty cycle decreases, thereby slowing the pump and reducing the pressure, across the filter 40. Conversely, as the input decreases, the duty cycle will be larger, and the pump speed will increase. Thus if the pressure at pump inlet 24 increases, the circuit senses the change and decreases the pump speed until the proper pressure is attained. If the pressure decreases, the circuit senses the change and increases the pump speed until the proper pressure is attained.

The proper level of pressure is determined by the output of op-amp U16 shown in FIG. 13. A reference voltage is placed on the non-inverting input of U16. It is this voltage that is amplified to varying degrees which determines the pressure level. Pressure regulation is accomplished by comparing the pressure generated by the pump to the voltage level provided by op-amp U16. As the voltage level increases, the motor will increase pump speed until the pressure meets the voltage level. This circuitry also compensates for barometric pressure when, for example, the system is taken from elevation 4500 feet to sea level. In this situation, the pump 22 will have a higher vacuum capability by as much as 15%. If the evacuation system has no compensation, the filter status display 62 would likely read clear (excessive air-flow) even when the display should indicate an obstructed filter. Compensation is accomplished by the pressure regulation circuitry. If the pressure produced by the pump 22 increases, the speed of the motor 20 is slightly decreased to offset the increased pressure. This adjustment will bring the generated pressure and airflow back to the intended level.

The foregoing descriptions of the illustrated electronic circuitry are intended to disclose practical circuits having components of practical values and are not intended to limit the scope of the appended claims, which are intended to define the illustrated embodiment and its equivalents.

What is claimed is:

1. A smoke evacuation system for removing surgically produced smoke, comprising:
   a support frame;
   a variable speed electric motor mounted on said frame;
   a vacuum pump having an inlet and an outlet mounted on said frame;
   means coupling said motor to said pump to drive said pump in response to operation of said motor;
   a filter to remove harmful components from surgically produced smoke, said filter having an inlet thereto and an outlet therefrom;
   first duct means having one end connected to the outlet of said filter and another end connected to said inlet of said vacuum pump;
   second duct means having one end connected to the inlet of said filter and a movable other end to be positioned in an area where smoke is surgically produced; and
   means for controlling the speed of said variable speed motor in accordance with the amount of smoke present at said movable other end of said second duct means.

2. A smoke evacuation system as in claim 1, further including manually set speed control means carried by the support frame and connected to said motor to control the speed of operation of said motor according to settings of said speed control means.

3. A smoke evacuation system as in claim 2, further including:
   pressure sensing means connected to the inlet of said vacuum pump and generating a signal indicative of the pressure at said inlet; and
   circuit means connecting said signal generated by said pressure sensing means to said variable speed motor and to vary the speed of said motor to maintain a substantially constant pressure as initially sensed by said pressure sensor upon actuation of said motor to a speed set by the speed control means.

4. A smoke evacuation system as in claim 2, further including sensor means for detecting the presence of smoke in said area, operably associated with said smoke responsive means.

5. A smoke evacuation system as in claim 2, further including selector switch means to selectively disconnect either the means for controlling the speed of said variable speed motor in accordance with the amount of smoke or the speed control means from control of the said variable speed motor.

6. A smoke evacuation system as in claim 5, further including:
   air flow detector means positioned in the path of air flow through said filter and said vacuum pump, said air flow detector operating a signal corresponding to the speed of air flow between said filter and said vacuum pump; and
   circuit means connecting said signal generated by said air flow detector to said variable speed motor to change the speed of said motor as required to change the speed of said pump to maintain the air flow detected by said air flow detector as established by said speed control means upon initial setting of said speed control means.

7. A smoke evacuation system as in claim 6, further including:
   pressure sensing means connected to the inlet of said vacuum pump and generating a signal indicative of the pressure at said inlet; and
   circuit means connecting said signal generated by said pressure sensing means to said variable speed motor and to vary the speed of said motor to maintain a substantially constant pressure as initially sensed by said pressure sensing means upon actuation of said motor to a speed set by the speed control means.

8. A smoke evacuation system as in claim 7, further including:
   a front panel carried by the support frame; and indicator means carried by said front panel, said indicator means indicating a filter status display means.

9. A smoke evacuation system as in claim 8, further including circuit means connecting said air flow detector means and said filter display means, whereby air flow detected by said flow detector means is displayed on said filter status display means as an indication of air flow through said filter.

10. A smoke evacuation system as in claim 9, further including circuit means connecting said pressure sensing means and said filter display means, whereby pressure detected by said pressure sensing means is displayed on said filter status display means as an indication of air flow through said filter.

11. A smoke evacuation system as in claim 8, wherein the indicator means carried by the front panel further includes means to indicate the on/off status of the variable speed motor.

12. A smoke evacuation system as in claim 11, wherein the indicator means carried by the front panel further includes means to indicate mode selection of the motor to an internal mode, wherein speed of said motor is controlled by a setting of said manually set speed control means or an external mode, wherein speed of said motor is controlled by said smoke responsive means.

13. A smoke evacuation system as in claim 12, wherein the indicator means carried by the front panel further includes means to indicate selected motor speed when the mode selection indicator indicates said motor to be in an internal mode.

14. A smoke evacuation system as in claim 5, further including means to default the speed control means to a setting for lowest motor speed upon initial actuation of said motor.

15. A smoke evacuation system as in claim 2, further including:
   air flow detector means positioned in the path of air flow from said filter through said vacuum pump, said air flow detector generating a signal corresponding to the speed of air flow between said filter and said vacuum pump; and
   circuit means connecting said signal generated by said air flow detector to said variable speed motor to change the speed of said motor as required to change the speed of said pump to maintain the air flow detected by said air flow detector as established by said speed control means upon initial setting of said speed control means.

16. A smoke evacuation system as in claim 15, further including:
   a front panel carried by the support frame; and
   indicator means carried by said front panel, said indicator means indicating a filter status display means.

17. A smoke evacuation system as in claim 16, further including circuit means connecting said air flow detector means and said filter display means, whereby air flow detected by said flow detector means is displayed on said filter status display means as an indication of air flow through said filter.

18. A smoke evacuation system as in claim 16, further including circuit means connecting said pressure sensing means and said filter display means, whereby pressure detected by said pressure sensing means is displayed on said filter status display means as an indication of air flow through said filter.

19. A smoke evacuation system as in claim 18, further including circuit means connecting said air flow detector means and said filter display means, whereby air flow detected by said flow detector means is displayed on said filter status display means as an indication of air flow through said filter.

20. A smoke evacuation system as in claim 19, wherein the indicator means carried by the front panel further includes means to indicate the on/off status of the variable speed motor.

21. A smoke evacuation system as in claim 20, wherein the indicator means carried by the front panel further includes means to indicate mode selection of the motor to an internal mode, wherein speed of said motor is controlled by a setting of said manually set speed control means or an external mode, wherein the speed of said motor is controlled by said smoke responsive means.

22. A smoke evacuation system as in claim 21, wherein the indicator means carried by the front panel further includes means to indicate selected motor speed when the mode selection indicator indicates said motor to be in an internal mode.

23. A smoke evacuation system as in claim 22, wherein the indicator means carried by the front panel further includes an error indicator to indicate failure of said smoke responsive means.

24. A smoke evacuation system as in claim 19, wherein the indicator means carried by the front panel further includes means to indicate mode selection of the motor to an internal mode, wherein speed of said motor is controlled by a setting of said manually set speed control means or an external mode, wherein the speed of said motor is controlled by said smoke responsive means.

25. A smoke evacuation system as in claim 19, wherein the indicator means carried by the front panel further includes means to indicate selected motor speed when the mode selection indicator indicates said motor to be in an internal mode.

26. A smoke evacuation system as in claim 19, wherein the indicator means carried by the front panel further includes an error indicator to indicate failure of the smoke responsive means for controlling the speed of said variable speed motor in accordance with the amount of smoke detected by said sensor means.

* * * * *